United States Patent [19]

Whitsett

[11] Patent Number: 5,387,746
[45] Date of Patent: * Feb. 7, 1995

[54] PULMONARY HYDROPHOBIC SURFACTANT-ASSOCIATED PROTEIN OF 6,000 DALTONS MOLECULAR WEIGHT AND MULTIMERS THEREOF

[75] Inventor: Jeffrey A. Whitsett, Cincinnati, Ohio

[73] Assignee: Scios Nova Inc., Mountain View, Calif.

[*] Notice: The portion of the term of this patent subsequent to May 7, 2008 has been disclaimed.

[21] Appl. No.: 975,202

[22] Filed: Nov. 12, 1992

Related U.S. Application Data

[63] Continuation of Ser. No. 857,685, Mar. 25, 1992, abandoned, which is a continuation of Ser. No. 695,961, Jun. 6, 1991, abandoned, which is a continuation of Ser. No. 504,691, Apr. 4, 1990, Pat. No. 5,013,720, which is a continuation of Ser. No. 860,239, May 6, 1986, abandoned.

[51] Int. Cl.$^6$ .................. A61K 37/02; C07K 7/10
[52] U.S. Cl. ............................. 514/12; 514/21; 435/69.1; 530/324; 530/350; 530/848
[58] Field of Search ............ 514/12, 21; 530/324, 530/350, 848; 435/69.1

[56] References Cited

U.S. PATENT DOCUMENTS

| | | | |
|---|---|---|---|
| 4,659,805 | 4/1987 | Schilling, Jt. et al. | 530/350 |
| 4,912,038 | 3/1990 | Schilling, Jr. et al. | 435/69.1 |
| 4,933,280 | 6/1990 | Schilling, Jr. et al. | 435/69.1 |
| 5,013,720 | 5/1991 | Whitsett | 514/12 |

OTHER PUBLICATIONS

Phizackerley, P. et al., *Biochem. J.*, 183: 731–736, 1979.
Glasser, S. et al., *JBC*, 263(1):9–12, 1988.
Glasser, S. et al., *JBC*, 263(21):10326–10331, 1988.
Whitsett, J. et al., *Pediatric Res.*, 20(5):460–467, 1986.
Whitsett, J. et al., *Pediatric Res.*, 20(8):745–749, 1986.
Claypool, W. et al., *Experimental Lung Research*, 6:215–222, 1984.
Takahashi, A., et al., *Biochem. Biophys. Res. Commun.*, 35(2):527–532, 1986.

Primary Examiner—Lester L. Lee
Attorney, Agent, or Firm—Morrison & Foerster

[57] ABSTRACT

A novel hydrophobic surfactant-associated protein mixture, i.e., a SAP-6 proteins, has been isolated from pulmonary animal tissue. A small, novel pulmonary hydrophobic surfactant-associated SAP-6-Val protein having a molecular weight of about 6,000 daltons as determined by SDS-PAGE and about 3,500–4,000 daltons as determined by tricine-SDS-PAGE has been further isolated from the SAP-6 protein mixture. The amino acid residue compositions of the SAP-6-Val protein for human and bovine have been determined and disclosed. When a SAP-6-Val protein is combined with phospholipids, it enhances the surfactant-like activity of the phospholipids in lungs of animals and, therefore, uniquely imparts to the mixture significant pulmonary biophysical activity. Such a mixture results in enhanced adsorption of the phospholipids with properties similar to that of natural pulmonary surfactant material. SAP-6-Val proteins in combination with phospholipids is highly useful for replacing or supplementing natural pulmonary surfactant material for reducing or maintaining normal surface tension in lungs, and especially in lungs of patients suffering from hyaline membrane disease, HMD, or other syndromes associated with the lack or insufficient amounts of natural pulmonary surfactant material. A mixture of a SAP-6-Val protein and phospholipids may be administered as an aerosol spray or in aqueous normal saline with or without calcium chloride for treating or preventing HMD and other surfactant deficiency states. Also disclosed are methods of isolating the non-canine SAP-6-Val proteins from the SAP-6 proteins isolated from animal tissue.

46 Claims, 1 Drawing Sheet

PULMONARY HYDROPHOBIC SURFACTANT-ASSOCIATED PROTEIN OF 6,000 DALTONS MOLECULAR WEIGHT AND MULTIMERS THEREOF

This application is a file wrapper continuation of application Ser. No. 07/857,685, filed Mar. 25, 1992, and now abandoned, which is a continuation of application Ser. No. 07/695,961, filed Jun. 6, 1991, and now abandoned which is a continuation of Ser. No. 07/504,691 filed Apr. 4, 1990 now U.S. Pat. No. 5,013,720 issued May 7, 1991, which is continued from Ser. No. 06/860,239 filed May 6, 1986 and now abandoned.

FIELD OF THE INVENTION

The present invention relates to isolated SAP-6-Val proteins, methods of isolating and using same and medicaments formed therewith.

BACKGROUND

Hyaline membrane disease, HMD, is a common disorder of premature infants and is related to diffuse atelectesis, hypoxia and resultant respiratory impairment. More particularly, HMD relates to the lack of vital pulmonary material necessary for reducing surface tension in the airways of the alveoli. As a result, the alveoli or terminal respiratory sacs of patients suffering from HMD normally collapse. And, because the surface tension at the gas-liquid interface in HMD patients is elevated, their alveoli or terminal respiratory sacs are very difficult to reinflate. Consequently, HMD may be associated with significant morbidity and mortality, especially in premature infants.

Present treatments of HMD focus on using high concentrations of oxygen, positive pressure and/or mechanical ventilation to maintain adequate oxygenation. These therapies are complicated by oxygen and pressure related injuries as well as injuries resulting from the need to mechanically access the airway via endotracheal tubes. More recent studies, however, have supported the use of replacement pulmonary surfactant material for therapy of HMD and other syndromes associated with the lack of pulmonary surfactant material. Such therapy has included heretofore the use of aerosolized or liquid synthetic phospholipid mixtures, natural pulmonary surfactant material and various preparations of surfactant material prepared from animal lung. Surface tension lowering ability of the naturally derived preparations is in general better than in the synthetic lipid preparations. Also, preliminary studies using modified bovine surfactants have been promising. Problems with human and animal pulmonary preparations, however, have occurred which include lack of variability, possible infection and immunologic risks. Obviously, when treating patients for any disease including HMD, it is imperative to include only those active substances necessary to minimize possible immunologic consequences of therapy to the patients. Unfortunately, because the natural pulmonary surfactant material and the preparations available heretofore are in crude form, they are less specific and associated with possibly greater immunologic risks.

Natural pulmonary surfactant material is a complex material composed primarily of phospholipids and surfactant-associated proteins or apolipoproteins. The phospholipids, mainly phosphatidylcholine (PC), disaturated phosphatidylcholine (DSPC) and phosphatidylglycerol (PG), are of paramount importance for the physiological role of natural pulmonary surfactant material in reducing surface tension in the alveoli. Phospholipids, of which DSPC is the principal component, are synthesized in the endoplasmic reticulum of Type II epithelial cells, packaged into lamellar bodies, then secreted into the alveolar space by an exocytotic process. Several of the phospholipids are apparently not catabolized and resynthesized, but rather it is presently believed that they are reutilized primarily as intact molecules and constitute the major components of the naturally existing pulmonary surfactant material.

With respect to the surfactant-associated proteins or apolipoproteins, there is considerable disagreement as to their identity and utility. Nonetheless, there is increasing agreement among those with medical expertise in this area that in addition to the lung surfactant phospholipids, at least some of these apolipoproteins are vital for the full biological activity of the natural pulmonary surfactant material in reducing surface tension in the alveoli.

Surfactant-associated proteins or apolipoproteins include both serum and lung specific proteins. The major lung specific surfactant-associated protein of 30–40,000 daltons identified in lung surfactant by King et al, Isolation of Apoproteins from Canine Surfactant Material, *Am J Physiol* 244:788–795, 1973, is a glycoprotein rich in glycine and containing collagen-like regions rich in hydroxyproline. This protein, herein called SAP-35, is synthesized from 28–30,000 dalton translation products which undergo glycosylation, hydroxylation of proline residues and sulfhydryl-dependent cross-linking to form large oligomers which can be detected in the airway. Proteolytic fragments of SAP-35 have been identified in protein preparations isolated from lavage of patients with alveolar proteinosis and from other mammalian surfactants migrating as proteins of small molecular weight by Whitsett et al, Characteristics of Human Surfactant-Associated Glycoprotein(s) A, *Pediatr Res* 19:501–508, 1985. While the glycoprotein SAP-35 binds phospholipids and may confer the structural organization of tubular myelin to surfactant lipids, it remains unclear whether SAP-35 is required for the biophysical activity of surfactants. See King et al, Metabolism of the Apoproteins in Pulmonary Surfactant, *J Appl Physiol* 42:483–491, 1977.

Smaller lung specific surfactant-associated proteins have also been identified from a variety of mammalian surfactants. King et al, *Am J Physiol* 223:715–726, 1972, previously described a 10,000–12,000 dalton protein in pulmonary surfactant material; however, the origin of this protein or its distinction from others was not clarified. This protein described by King et al is now believed to be a fragment of the major glycoprotein SAP-35. Smaller surfactant-associated proteins, other than that reported by King et al, have been identified in alveolar lavage material from a number of species and with molecular weights of approximately 10,000 daltons in dog and rabbit, 10,500–14,000 daltons in rat, 11,500–16,500 daltons in pig, and 10,000 daltons in cow.

The nature and relationships among these various surfactant-associated proteins (SAPs) and the larger protein, SAP-35 or its fragments, have not been established. Nevertheless, the work of Suzuki et al, *J Lipid Res* 23:53–61, 1982, suggested that a small 15,000 daltons protein in pig alveolar lavage had a greater affinity for lipid than SAP-35. Suzuki et al unfortunately did not distinguish the proteins from the SAP-35 or its fragments or demonstrate if there exists surfactant properties in a purified state. Rather, Suzuki et al only suggested that this 15,000 dalton protein is possibly a physiological regulator for the clearance of alveolar phospholipid. Claypool et al, *J Clin Invest* 74:677–684, 1984, suggested that a small unidentified protein, isolated from rat alveolar lavage, increased the uptake of liposomes by cultured Type II epithelial cells. Work by Wang et al, Amino Acid Composition of Low Molecular Weight Hydrophobic Surfactant Apoproteins, *Fed Proc* 44:1024 (abstract), 1985, described two distinct small molecular weight proteins in surfactant from rat that are ethanol soluble. But like Suzuki et al, Wang et al failed to purify, identify activity, or characterize the protein to homogeneity. Wang et al instead suggested that these small molecular weight proteins may be involved with surfactant recycling. It also has been suggested that the smaller molecular weight proteins, such as those discussed above, possibly arise as proteolytic fragments of the larger SAP-35 molecule. At present, however, it is unclear whether SAP-35, one or more of the smaller proteins, or all proteins together are active components imparting biophysical activity to natural mammalian pulmonary surfactant material.

In view of the present state of the art, there obviously are needs to clarify the nature and role of the surfactant-associated lung specific proteins and to determine the most effective means for treating and preventing HMD and other syndromes associated with lack or insufficient amounts of pulmonary surfactant material to maximize HMD therapy and to eliminate the disadvantages associated with HMD therapy available heretofore.

SUMMARY OF THE INVENTION

In brief, the present invention alleviates and overcomes the above problems and shortcomings of the present state of the art through the discovery of a novel hydrophobic surfactant-associated proteins isolated from animal tissue, hereinafter "SAP-6 proteins". The novel SAP-6 proteins comprise two hydrophobic surfactant-associated proteins. It has been discovered that when the SAP-6 proteins are combined with phospholipids to form a novel preparation, such preparation has significant pulmonary biophysical surfactant activity that can be utilized to effectively treat and prevent HMD and other syndromes associated with the lack or insufficient amounts of natural pulmonary surfactant material. Although it is presently believed that the SAP-6 proteins are lung specific, their pulmonary biophysical surfactant activity is believed not to be species specific. The SAP-6 proteins therefore can be purified from animal tissue, specifically pulmonary tissue or amniotic fluid, extracted from a variety of animals, such as canine, bovine, human, porcine, rabbit, rat and the like. Notwithstanding, the concentrations of the SAP-6 proteins in pulmonary tissue and lavage are probably greater than that found in amniotic fluid. With respect to other animal tissues or fluid, however, the SAP-6 proteins are believed to be absent or present in substantially smaller or undetectable concentrations.

In a further discovery, a novel SAP-6-Val protein has been isolated from a mixture of the SAP-6 proteins in substantially pure form, as described hereinafter. The novel SAP-6-Val protein is termed SAP-6-Val on the basis of an unique polyvaline domain. The novel SAP-6-Val protein comprises approximately 33–38 amino acid residues and includes within its protein structure a hydrophobic region rich in valine residues. The hydrophobic region of the SAP-6-Val protein is believed to play an important role in the association of the SAP-6-Val protein with membranes, and it is within this hydrophobic region that the unique polyvaline domain resides. The polyvaline domain originally contains a first stretch of about 6 adjacent valine residues and a second stretch of about 3 adjacent valine residues separated from the first stretch by about 2 hydrophobic amino acid residues. The hydrophobic region and stretches of adjoining valine residues are uniquely and inherently characteristic for the SAP-6-Val proteins and are believed to be common to different species, as depicted by the sequences identified for human, bovine and canine reported hereinafter.

In a yet further discovery, it has been realized that when the SAP-6 proteins are initially isolated in a mixture from animal tissue, it comprises the SAP-6-Val protein and a second hydrophobic SAP-6 dalton surfactant-associated protein, as well as multimers of both such proteins. Once the SAP-6-proteins have been isolated from animal tissue, the two SAP-6 proteins can be quite easily separated from the larger multimers thereof by, for instance, gel electrophoresis migration. And, based upon this gel separation technique, it is believed that the two SAP-6 proteins and in particular the SAP-6-Val protein constitute the predominant components of the mixture of isolated SAP-6 proteins. When utilizing gel electrophoresis migration in the absence of sulfhydryl reducing agents, however, increased amounts of the larger, hydrophobic protein multimers are detected.

The simple molecular weights of the two SAP-6 proteins, i.e., the SAP-6-Val protein and the other hydrophobic SAP-6 protein of the SAP-6 mixture, are about 6,000 daltons for SAP-6-Val and about 6,000 daltons for the other SAP-6 protein as determined in a polyacrylamide gel containing sodium dodecyl sulfate (SDS-PAGE). The molecular weights for the larger, protein multimers are about 14,000, about 20,000 and about 26,000 daltons in SDS-PAGE. While the simple molecular weight for the SAP-6-Val protein is about 6,000 daltons in SDS-PAGE, it is about 3,500–4,000 daltons in tricine-SDS-PAGE. It should be readily apparent to those versed in the art, however, that since gel electrophoresis migration has been employed to determine the molecular weights for these novel proteins, the molecular weights are only estimates based upon relative migrations.

The SAP-6 proteins and the larger, hydrophobic protein multimers thereof can be further characterized as having the ability to enhance the surfactant-like activity of phospholipids in lungs of animals, and as being substantially resistant to protease enzymes, endoglycosidase F, and collagenase. Furthermore, it is believed that when the SAP-6 proteins are combined with phospholipids, the SAP-6 proteins uniquely enhance the surfactant properties of the phospholipids thus imparting to the combination significant pulmonary biophysical surfactant activity. Likewise, when the SAP-6-Val protein is combined with phospholipids, the SAP-6-Val protein has the unique ability to enhance the surfactant-like activity of phospholipids. As a result of this remarkable property, such combinations are highly useful for replacing or supplementing natural pulmonary surfactant material for reducing or maintaining normal surface tension in the lungs, especially in the lungs of patients suffering from HMD and other syndromes associated with the lack or insufficient amounts of natural pulmonary surfactant material. And, since the SAP-6 proteins and especially the SAP-6-Val proteins of this invention can be highly purified from animal tissue, the immunologic risks currently associated with the less pure preparations available heretofore for treating or preventing HMD or related syndromes are substantially reduced.

In accordance with another discovery of the present invention and as earlier reported herein, it is believed that there are at least two hydrophobic surfactant-associated proteins which form the SAP-6 mixture, and that such proteins have the unique ability to enhance the surfactant-like activity of phospholipids in lungs of animals. It is presently believed that these two hydrophobic proteins, i.e., the SAP-6-Val 6,000 dalton protein and the other SAP-6 6,000 dalton hydrophobic surfactant-associated protein, co-elute together, co-purify together via gel electrophoresis migration in SDS-PAGE, and have similar biophysical properties. Therefore, it is to be understood that the terms "surfactant-associated protein," and "SAP-6 protein(s)" are used interchangeably herein and that, whenever referenced herein, they are meant to include any small hydrophobic surfactant-associated protein that has the unique ability to enhance the surfactant-like activity of phospholipids in lungs of animals, that has a simple molecular weight of about 6,000 daltons determined by SDS-PAGE and which is substantially resistant to protease enzymes, endoglycosidase F and collagenase.

The present invention further resides in a method of separating from animal tissue the novel SAP-6 proteins which involves separating the animal tissue into a particulate fraction and a liquid fraction, and extracting from the liquid fraction the novel SAP-6 proteins in a substantially pure state. The methods of this invention are further concerned with separating the SAP-6-Val protein from the mixture of SAP-6 proteins, for instance, via dialysis, and also separating the larger, novel hydrophobic multimers from the SAP-6 proteins. As already mentioned above, multimer separation can be accomplished by, for instance, gel electrophoresis migration or other suitable techniques.

The present invention still further contemplates novel medicaments, preparations and methods employed to treat animals, including human infants, suffering from HMD and other syndromes related to the lack or insufficient amounts of natural pulmonary surfactant material. Also contemplated by the present invention are novel antibodies and antisera directed against the SAP-6 proteins and multimers thereof.

Accordingly, it can be appreciated that the present invention provides a solution to the art that has long sought to understand natural pulmonary surfactant material and effective means to treat or prevent HMD and other syndromes associated with the lack or insufficient amounts of natural pulmonary surfactant material.

The above features and advantages will be better understood with reference to the Figures, Detailed Description and Example set out hereinbelow. It will also be understood that the compositions and methods of this invention are exemplary only and are not to be regarded as limitations of this invention.

BRIEF DESCRIPTION OF THE FIGURES

Reference is made to the accompanying Figures in which is shown isolated from hydrophobic surfactant-associated protein factor SAP-6 and multimers thereof.

DETAILED DESCRIPTION OF THE INVENTION

By way of illustrating and providing a more complete appreciation of the present invention and many of the attendant advantages thereof, the following detailed description is provided concerning the novel SAP-6 proteins, the novel SAP-6-Val protein, the novel medicaments, the novel antibodies and antisera, and the novel methods of isolation and utilization thereof.

The present invention provides novel, hydrophobic surfactant-associated SAP-6 proteins isolated from animal tissue, specifically from pulmonary tissue and amniotic fluid. The novel SAP-6 proteins consists essentially of two small, novel hydrophobic surfactant-associated proteins, i.e., the SAP-6-Val protein and a second hydrophobic SAP-6 protein, and larger, hydrophobic protein multimers of both such proteins. The SAP-6 proteins have simple molecular weights of about 6,000 daltons and the larger, hydrophobic protein multimers thereof have molecular weights of about 14,000, about 20,000 and about 26,000 daltons as determined by SDS-PAGE. As earlier reported herein, one SAP-6 protein i.e., the SAP-6-Val protein, also has a simple molecular weight of about 3,500-4,000 daltons as determined by tricine-SDS-PAGE. It should be realized that other multimers may exist but in smaller undetectable concentrations. As used herein, "simple molecular weight" refers to the molecular mass of what is thought to be the smallest polypeptide chain after sulfhydryl reduction which serves as a repeating building block for a multimer.

To determine the molecular weights and separate the SAP-6 proteins from the larger multimers, for instance, a gel formed with about 3-27% polyacrlyamide, in particular about 15% polyacrylamide (PAGE), and about 2% of sodium dodecyl sulfate (SDS) can be used to separate and determine the molecular weights of the novel proteins in SDS-PAGE gel. See FIG. 1. For comparison, low molecular weight protein markers such as trypsin inhibitor (6,200), lysozyme (14,000), beta-lactalbumin (18,400), alpha-chymotrypsin (25,700) and ovalbumin (43,000) can be used. These can be obtained from BRL, Inc., of Bethesda, Md. Although the SAP-6 proteins are detected in relatively greater amounts than the multimers, an increase is observed in the larger protein multimer forms when the gel separation is performed on the SAP-6 proteins in the absence of sulfhydryl reducing agents, such as beta-mercaptoethanol, dithiothreitol (DTT), or after reduction and alkylation. Presently, it is believed sulfhydryl bonding, non-sulfhydryl aggregation and/or interpeptide bonding of a fraction of the SAP-6 proteins account for the larger, hydrophobic multimer forms. As earlier discussed in the summary section hereof, it should be understood that the molecular weights are only estimates based upon relative migrations and that other suitable techniques may be employed to ascertain the molecular weights.

Throughout the specification, the SAP-6 proteins including the larger multimers thereof, collectively as "SAP-6 proteins," are characterized as being hydrophobic and surfactant-associated proteins. As used herein, "hydrophobic," refers to solubility in non-polar solvents, such as 3:1 ether/ethanol, chloroform, chloroform/methanol in various ratios, such as 3:1, and having an abundance of hydrophobic non-charged amino acids. The terms "SAP-6 protein," and "surfactant-associated protein," as used herein, refers to proteins associated with binding to or co-purifying with the phospholipid components of mammalian surfactants during centrifugation in isotonic solution. With respect to the term "multimer" as used herein in connection with the larger hydrophobic proteins, it refers to either covalent or non-covalent aggregates of 6,000 dalton SDS-PAGE SAP-6 proteins which form oligomers of varying molecular weights, such as dimers, trimers, quatramers, etc.

SAP-6 proteins can be further characterized as being substantially resistant to protease enzymes (trypsin, chymotrypsin and staph V-8), endoglycosidase F, and collagenase. It has been discovered that SAP-6 proteins are not degraded nor are their sizes or size heterogeneities significantly altered by these enzymes.

In further characterizing the SAP-6 proteins, they are found to have unique localization in lamellar bodies of pulmonary type II cells and surfactant in a variety of mammalian species as well as human amniotic fluid near term gestation.

With respect to the determination of the amino acid composition of a SAP-6 protein, reduced and alkylated purified samples are hydrolyzed in about 300 microliters of constant boiling 5.7N HCl containing 0.3% phenol and 0.01% beta-mercaptoethanol at about 150° C. under vacuum for about 24 hours. The amino acids are determined using a Beckman 6300 amino acid analyzer with a SICA 7000A Integrator.

Table I illustrates the amino acid compositions that have been determined for a bovine SAP-6-Val protein and a canine SAP-6-Val protein. It should be understood to those skilled in the art that since the amino acid compositions have been determined using a Beckman 6300 analyzer, the amino acid residue compositions per protein molecule are only estimates based upon this analytical technique.

TABLE I

Approximate Amino Acid Compositions of SAP-6-Val Proteins

| Amino Acid Residues | Amino Acid Residues Per Protein Molecule | |
|---|---|---|
| | Bovine | Canine |
| Cysteine (CM—Cys) | about 3.6 | about 1.6 |
| Aspartic acid (ASX) | about 2.1 | about 0.5 |
| Threonine (The) | about 0.2 | about 0.3 |
| Serine (Ser) | about 0.6 | about 4.0 |
| Glutamic acid or | about 0.3 | about 0.4 |

TABLE I-continued

Approximate Amino Acid Compositions of SAP-6-Val Proteins

| Amino Acid Residues | Amino Acid Residues Per Protein Molecule | |
|---|---|---|
| | Bovine | Canine |
| Glutamine (Glx) | | |
| Proline (Pro) | about 4.3 | about 4.6 |
| Glycine (Gly) | about 4.1 | about 5.1 |
| Alanine (Ala) | about 2.3 | about 2.3 |
| Valine (Val) | about 23.1 | about 19.2 |
| Methionine (Met) | about 1.8 | about 1.7 |
| Isoleucine (Ile) | about 4.7 | about 5.9 |
| Leucine (Leu) | about 13.8 | about 13.9 |
| Tyrosine (Tyr) | about 0.2 | — |
| Phenylalanine (Phe) | about 0.3 | about 1.9 |
| Histidine (His) | — | — |
| Lysine (Lys) | about 2.0 | about 2.0 |
| Tryptophan (Trp) | — | — |
| Arginine (Arg) | about 1.9 | about 2.0 |
| Estimated Mol. Wt. on SDS-PAGE of dimers of SAP-6-Val proteins | 6588 | 6441 |

CM—Cys = carboxymethyl cysteine.

Two distinct SAP-6 proteins essentially form the SAP-6 mixture of the instant invention, i.e., a SAP-6-Val protein and a 6,000 dalton hydrophobic surfactant-associated protein. In accordance with this invention, the SAP-6-Val protein has been isolated from the SAP-6 mixture in virtually pure form and identified herein. The predicted sequence for a human SAP-6-Val protein and the partial $NH_2$-terminal end amino acid sequences of SAP-6-Val proteins isolated from human, bovine and canine tissue are also characterized hereinbelow.

The SAP-6-Val protein is termed SAP-6-Val on the basis of an unique polyvaline domain. The SAP-6-Val protein is believed to be comprised of approximately 33-38 amino acids and is thought to either begin with the amino acid residue isoleucine (Ile), phenylalanine (Phe) or glycine (Gly) following the $NH_2$-terminal residue or include the amino acid residue isoleucine (Ile) within the first few residues following the $NH_2$-terminal residue. Since the SAP-6-Val protein is derived from larger precursor proteins, proteolytic processing of the precursor proteins for SAP-6-Val can result in different amino acid residues located adjacent the $NH_2$-terminal residue. For example, leucine (Leu), phenylalanine (Phe) and glycine (Gly) have been detected in the first cleavage of SAP-6-Val proteins. Thus, it should be understood that SAP-6-Val may include isoleucine (Ile), phenylalanine (Phe), glycine (Gly), leucine (Leu), arginine (Arg), etc. as one of the first amino acid residues immediately following the $NH_2$-terminal residue. With respect to the amino acid residues located near the C-terminal end of a SAP-6-Val protein, their precise characterization remains unclear. Nevertheless, approximately 33-38 amino acid residues are thought to extend between the C-terminal and $NH_2$-terminal residues.

A SAP-6-Val protein of the instant invention includes a hydrophilic region extending from the N-terminal residue and a hydrophobic region of approximately 25 amino acids extending between the $Leu_{11}$ and $Leu_{33}$ residues, as indicated by the sequence below. This hydrophobic region of about 25 amino acid residues is valine-rich, as suggested by the SAP-6-Val proteins tabulated in Table I and the sequences reported below, and is believed to play an important role in the association of the SAP-6-Val protein with membrane. The hydrophobic region contains a first stretch of about 6 adjacent valine amino acid residues and a second stretch of about 3 adjacent valine amino acid residues which are separated from one another by about 2 hydrophobic amino acid residues, such as leucine (Leu), isoleucine (Ile) and valine (Val). The hydrophobic region and stretches of adjoining valine residues are uniquely and inherently characteristic for the SAP-6-Val protein and are believed to be common to different species, as depicted by the sequences identified for human, bovine and canine below.

While the molecular weight of SAP-6-Val as determined by SDS-PAGE is about 6,000 daltons, its molecular weight is about 3,500–4,000 daltons when determined by tricine-SDS-PAGE. This lower molecular weight for SAP-6-Val is also confirmed by the types and number of amino acid residues, i.e., about 33–38, in the composition of SAP-6-Val.

The discrepancy in the electrophoretically determined molecular weights of SAP-6-Val is believed to be due in part to the superior resolution capability of the tricine-SDS-PAGE technique. The heterogeneity of the size of the SAP-6-Val protein in SDS-PAGE may result from the fact that SAP-6-Val may form aggregates or oligomers which migrate as larger forms as determined by SDS-PAGE. Regardless of which electrophoretic technique is selected to determine the molecular weight of SAP-6-Val, however, both molecular weights represent inherent identifying characteristics for SAP-6-Val as isolated in accordance with the methods of this invention.

As already indicated above, the predicted amino acid sequence for SAP-6-Val protein is thought to begin at the Ile amino acid residue or at a few amino acid residues before the Ile amino acid residue and extend to about the $Leu_{33}$ amino acid residue. The hydrophobic domain of amino acids including amino acid residues $Leu_{11}$ to $Leu_{33}$ is thought to be compatible with a membrane-associated region of approximately 25 amino acids. This hydrophobic region contains the characteristic stretches of repeating valine residues. A predicted amino acid sequence for a human SAP-6-Val protein is as follows:

—Ile—Pro—Cys—Cys—Pro—Val—His—
—(Phe)—(Gly)
   (Arg)

Leu—Lys—Arg—$Leu_{11}$—Leu—Ile—Val—

Val—Val—Val—Val—Val—Leu—Ile—

Val—Val—Val—Ile—Val—Gly—Ala—

Leu—Leu—Met—Gly—$Leu_{33}$.

Presently, the sequences for what is believed to be the first 18, the first 25 and the first 23 amino acid residues following the amino-terminal residue for a SAP-6-Val human, bovine and canine protein, respectively, as ascertained from standard sequencing techniques, are as follows.

For human, the first 18 amino acid residues after the amino-terminal residue are —Ile—Pro—Cys—Cys—Pro—
(Ile)    (Pro)
(Leu)

Val—Asn—Leu—Lys—Arg—
           (His)

Leu—Leu—Ile—Val—Val—

Val—Val—Val.

Thus, in view of the above amino acid sequences for the human SAP-6-Val protein, it should be appreciated that the human SAP-6-Val sequence may comprise —Ile—Pro—Cys—Cys—Pro—
—(Phe)—(Gly) (Pro)
   (Arg)
   (Ile)
   (Leu)

Val—His—Leu—Leu—Arg—$Leu_{11}$—Leu
           (Asn)

Ile—Val—Val—Val—Val—Val—Val

Leu—Ile—Val—Val—Val—Ile—Val

Gly—Ala—Leu—Leu—Met—Gly—$Leu_{33}$.

The amino acid residues designated in parentheticals above and herein throughout represent optional or alternate or unconfirmed amino acid residues.

For bovine, the first 25 amino acid residues after the amino-terminal residue are Leu—Ile—Pro—Cys—Cys—

Pro—Val—Asn—Ile—Lys—

Arg—Leu—Leu—Ile—Val—

Val—Val—Val—Val—Val—

Leu—Leu—Val—Val—Val—
(Val) (Val)

For canine, the first 22 amino acid residues after the amino-terminal residue are Ile—Pro—Cys—Phe—Pro—

Ser—Ser—Leu—Lys—Arg—

Leu—Leu—Ile—Ile—Val—

Val—Val—Val—Val—Val—
         (Ile) (Ile)

Val—Val.

In the above sequences, the amino acid residues having alternately designated amino acid residues in parentheticals underneath are not yet confirmed.

In sequencing the SAP-6 proteins and in particular SAP-6-Val human, bovine and canine proteins, the following procedure may be utilized.

Samples of purified SAP-6 proteins are prepared by Edman sequence analysis by first dialyzing the samples against water. The samples are taken up in methanol and applied to a glass fiber filter. The analysis is performed on an Applied BioSystems model 470A Gas Phase Protein Sequencer. Analysis of the resulting phenylthiohydantoins (PTH) is accomplished by high pressure liquid chromatography (HPLC) at 50° C. on an Altex reversed-phase PTH-$C_{18}$ column. A binary buffer system consisting of ammonium acetate buffered acetonitrile, pH of 4.5, is used.

The chromatography procedure is conducted utilizing buffer A which contains about 10% acetonitrile and buffer B which contains about 90% acetonitrile. The initial chromatography conditions are 70% buffer A and 30% buffer B with a flowrate of 1.0 ml per minute. One minute after injection, the concentration of buffer B is linearly increased to 50% over a 3 minute period and held at this level for 8 minutes. The concentration of Buffer B then is reduced to 30% over one minute. After re-equilibration, which takes approximately 10 minutes, another PTH sample is injected. A discussion of this separation procedure appears in greater detail in Joseph L. Meuth and J. Lawrence Fox, Separation of Amino Acid Phenylthiohydantoin Derivatives by High-Pressure Liquid Chromatography, Analytical Biochem, 154(2):478–484, 1986, which is incorporated herein by reference in its entirety.

The sequence for the first 14 amino acid residues after the amino-terminal residue for the other human 6,000 dalton SAP-6 protein isolated from human tissue origin has also been ascertained in accordance with the above described sequencing techniques and is as follows:

Phe—Pro—Ile—Pro—Leu—

Pro—Tyr—Cys—Trp—Leu—

Cys—Arg—Ala—Leu.

Figure 1:
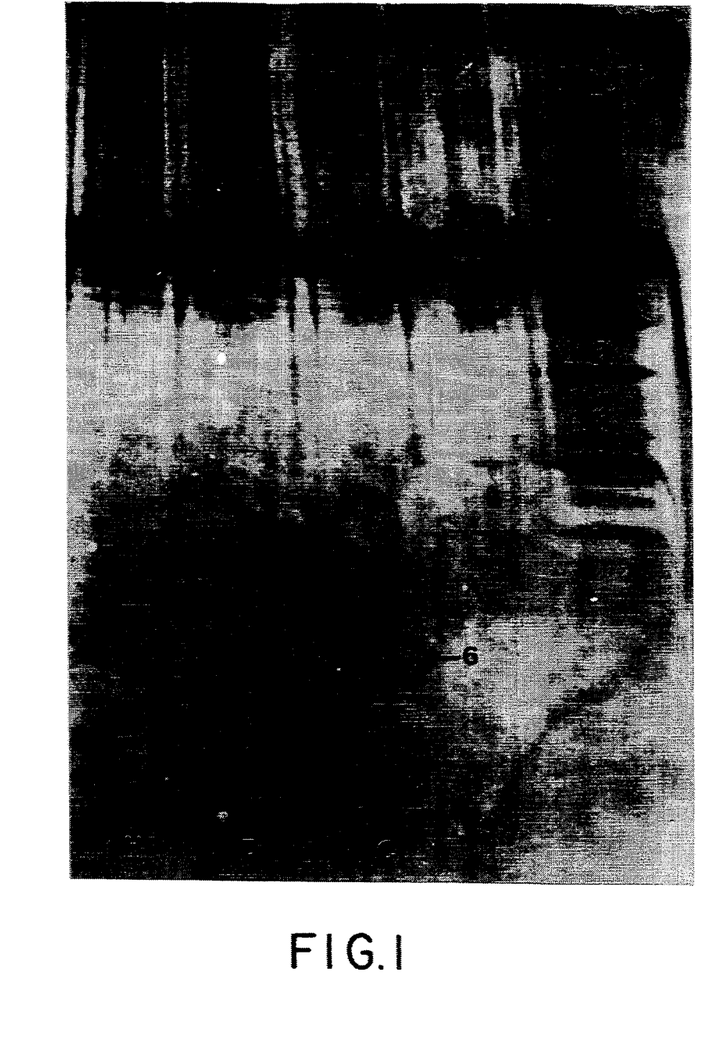
FIG. 1. SAP-6 proteins from human, canine and bovine. SAP-6 proteins were purified and delipidated as described herein and applied to 10-20% sodium dodecyl sulfate-polyacrylamide gel electrophoresis gels in the presence of beta-mercaptoethanol. Each lane represents approximately 2 micrograms of each protein detected by silver staining. Purified SAP-6 proteins from each species, H=human, D=canine, and C=bovine, migrated at $Mr=6,000$ and 14,000. The beta-mercaptoethanol artifact is also observed at $Mr=65-70,000$. Standard molecular weight markers are seen on the right.
Figure 2:
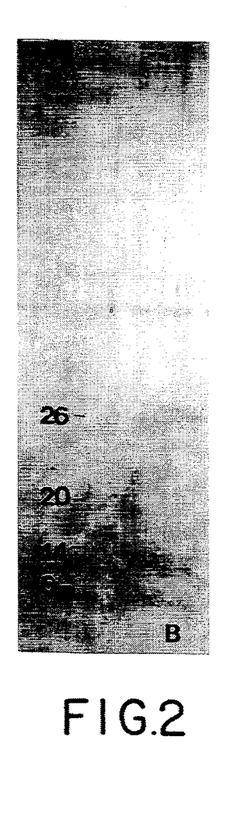
FIG. 2. SAP-6 proteins from bovine. SAP-6 proteins were purified and delipidated as described herein and applied to 10-20% sodium dodecyl sulfate-polyacrylamide gel electrophoresis gels in the absence of beta-mercaptoethanol. Lane B represents approximately 2 micrograms of protein detected by silver staining. Purified SAP-6 proteins from bovine, Lane B, migrated at $Mr=6,000$, and lesser amounts at 14,000, 20,000 and 26,000.

As already indicated and suggested by the above human $NH_2$-terminal sequence, there is believed to exist more than one 6,000 dalton hydrophobic surfactant-associated protein. With respect to these SAP-6 proteins, the following has been observed. First, the N-terminal amino acid residue sequences of the SAP-6-Val proteins for human, bovine and canine species, although similar to one another as indicated above, appear to be substantially different from the other N-terminal amino acid residue sequence of the human species set forth immediately above. Secondly, when the SAP-6 proteins are subjected to SDS-PAGE gel electrophoresis migration in the absence of beta-mercaptoethanol, a sulfhydryl reducing agent, major and minor amounts of protein appear. This can be better understood with reference to FIG. 1 wherein major amounts of silver stained protein exist at the 6,000 and 14,000 molecular weight migratory regions whereas only minor amounts of silver stained protein exist at the 20,000 and 26,000 molecular weight migratory regions. Thirdly, when the SAP-6 proteins are subjected to gel electrophoresis migration in the presence of beta-mercaptoethanol, silver stained proteins appear only at the 6,000 and 14,000 molecular weight migratory regions as shown in FIG. 2. In view of the above noted observations, it is presently believed that more than one SAP-6 protein exists. More particularly, it is thought that two separate and distinct SAP-6 proteins exist, i.e., a SAP-6-Val protein and a second 6,000 dalton SDS-PAGE hydrophobic surfactant-associated SAP-6-protein, and it is further believed that they co-elute together, co-purify together via SDS-PAGE gel electrophoresis migration, have similar molecular weights of about 6,000 daltons as determined in SDS-PAGE, have similar biophysical surfactant-like activity, and have similar enzyme resistance. Further, it is believed that the larger multimers, i.e., $Mr=20,000$ and $Mr=26,000$, of one or more of the 6,000 dalton SAP-6 proteins are possibly bonded together via sulfhydryl bonds in view of their migration patterns in the absence and presence of beta-mercaptoethanol, as illustrated in FIGS. 1 and 2. Therefore, it should be understood that any 6,000 dalton hydrophobic surfactant-associated protein, i.e., a SAP-6 protein, is well within the contemplation of this invention.

The present invention further relates to a novel method for isolating the novel SAP-6 proteins. The novel SAP-6 proteins can be purified from, for example, animal tissue and fluids, cells, cultivated cells, suitable pulmonary surfactant replacement preparations available, such as CLSE or Surfactant-TA, and the like. It should be appreciated therefore that the expression "animal tissue" as used herein is meant in a broad sense to encompass all appropriate sources for the SAP-6 proteins, including but not limited to animal tissue and fluid, cells, cultivated cells, pulmonary surfactant replacement preparations, such as CLSE and Surfactant-TA, and the like. It is preferred, however, to isolate the SAP-6 proteins from animal pulmonary tissue or amniotic fluid, and more preferably human pulmonary tissue. Solutions containing the novel SAP-6 proteins are obtained by extraction of animal tissue in which these proteins occur. For instance, after the mammalian lung is excised, the trachea preferably should be cannulated and washed repeatedly with several volumes of an iced, buffered solution, such as, (pH 7.0–7.4) 0.9% NaCl, to remove surfactant from the alveoli. The wash is centrifuged at low speed, for example, $1,000 \times g$ for ten minutes, and should be repeated if necessary to remove contaminating blood and white cells or macrophages. All procedures preferably should be performed at about 2°–4° C. This surfactant material should then be centrifuged at high speed from the alveoli wash to sediment particulate materials at about $10,000 \times g$ for about 30 minutes or longer. This pellet preferably should be resuspended and washed by repeated centrifugation and sonicated or freeze thawed, several times if necessary, in a suitable buffer, such as the one above, to uniformly resuspend the materials.

The resulting white surfactant is pelleted by centrifugation, the aqueous material is removed and is extracted with about 10–100 volumes of approximately 2:1 ether/ethanol, 3:1 chloroform/methanol or other suitable organic solvents at about $-30°$ C. to produce a supernatant containing the SAP-6 proteins. Extractions should proceed over night. The material should then be centrifuged again at about $10,000 \times g$ for about 20 minutes or longer. The resulting liquid fraction will contain lipid and include the novel, SAP-6 proteins of this invention. The liquid fraction thereafter can be dried (concentrated) with, for instance, $N_2$ stream, resuspended in an organic solvent, such as chloroform or other suitable organic solvents, and applied to a silicic acid column or LH-20 column, approximately 50 cm $\times$ 2.5 cm in size which is pre-equilibrated with chloroform or other suitable organic solvents at room temperature. The column is then eluted with, for example, 50 to 200 mls of a mixture of chloroform and alcohol, such as methanol or the like, increasing the alcohol concentration from 0% to about 100% in stepwise or gradient fashion. The SAP-6 proteins are eluted in the solvents containing alcohol having concentrations of greater than about 40% up to about 100% and more particularly about 40% to about 80%. Most of the lipids present in the SAP-6 proteins will be separated from the proteins at this stage. It should be appreciated to those skilled in the art that the silicic acid column can also be eluted with any other suitable solvents capable of extracting therefrom the hydrophobic SAP-6 proteins of this invention. Fractions containing mixtures of the SAP-6 proteins of this invention now can be assessed by, for example, fluorescamine assay and gel electrophoresis migration (SDS-PAGE or tricine-SDS-PAGE) followed by staining with silver stain or Coomassie staining. The SAP-6 proteins isolated at this point is considered to be substantially pure and homogeneous. By "substantially pure" it is meant herein that the SAP-6 proteins present therein are substantially free of contaminants, such as cells, cellular debris, DNA, RNA, and major surfactant glycoproteins or fragments thereof. It should be appreciated, however, that some lipids still remain in the now substantially pure protein factor.

To produce virtually pure SAP-6-Val protein, the fractions containing the mixtures of eluted SAP-6 proteins preferably are pooled, evaporated to near dryness and subjected to repeated dialysis in, for example, a cellulose dialysis bag with about 100–500 volumes of about 2:1 of chloroform/methanol or other suitable mixtures or acidified chloroform/methanol mixtures acidified with HCl or other appropriate acids at about room temperature. This procedure should proceed until the SAP-6-Val protein is virtually free of contaminating lipids and other SAP-6 proteins. This substantially purified SAP-6-Val protein can also be assessed by fluorescamine assay and gel electrophoresis migration. It should be realized that other suitable delipidating steps may also be employed to accomplish the above delipidating objective. The approximate amino acid composition can now be determined and the SAP-6-Val protein can be identified after PAGE with Coomassie, silver staining or other standard staining techniques. It should be appreciated that the above methods are described in generality and can be utilized with other suitable solvents and methods to separate the novel SAP-6 proteins from appropriate sources, and to further separate the novel SAP-6-Val protein from the SAP-6 proteins.

It should now be well apparent to those versed in the art that SAP-6 proteins and the SAP-6-Val protein can be isolated from several animals and in particular human animals and, once sequenced, can be synthesized by direct peptide synthesis or by genetic engineering-technology to provide adequate synthetic material required for medicinal and research use. A discussion of the SAP-6 proteins appears in Whitsett et al, Hydrophobic Surfactant-Associated Protein (SAP 6-14). In Whole Lung Surfactant and Its Importance for Biophysical Activity in Lung Surfactant Extracts Used for Replacement Therapy, *Pediatr Res,* 20(5):460–467, 1986, and Whitsett et al, Immunologic Identification of a Pulmonary Surfactant-Associated Protein of Mr=6,000 daltons, *Pediatr Res,* 20(8):744–749, 1986, in which these articles are incorporated herein by reference in their entireties.

It is believed that the SAP-6 proteins of this invention have useful "surfactant-like activity". As used herein, "surfactant-like activity" refers to the ability to interact with phospholipids to reduce surface tension spread on a surface and/or reduce surface tension at an air/liquid interface. When the SAP-6 proteins and in particular the purified SAP-6-Val proteins are mixed with phospholipids, their unique ability to enhance the surfactant-like activity of phospholipids in lungs of an animal is believed to impart to the mixture significant pulmonary biophysical surfactant activity. Such a mixture with this activity is highly useful for replacing or supplementing natural pulmonary surfactant material for reducing or maintaining normal surface tension in lungs, especially in the lungs of animals suffering from HMD and other syndromes associated with the lack or insufficient amounts of natural pulmonary surfactant material.

To prepare a preparation for medicinal application comprising a mixture of the SAP-6 proteins or purified SAP-6-Val proteins and phospholipids, a mixture of isolated SAP-6 proteins or purified SAP-6-Val proteins can be stored in chloroform under nitrogen or air at about $-30°$ C. prior to reconstitution with phospholipids. The phospholipids that may be employed can be derived from a number of suitable phospholipids, such as phosphatidylcholine, disaturated phosphatidylcholine, phosphatidylglycerol, dipalmitoylphosphatidylcholine, phosphatidylinositol and mixtures thereof and the like. For example, isolated SAP-6 proteins or purified SAP-6-Val proteins can be mixed in an amount of about 0.1 to about 2.0% with synthetic phospholipids, such as about 65% dipalmitoylphosphatidycholine, about 20% egg-phosphatidycholine, about 7.5% of soy-phosphatidylinositol, and about 7.5% egg-phosphatidylglycerol. If desired, in preparing such a medicament, the mixture may further contain a physiological buffer comprising 0.9% sodium chloride with or without about 0.5 to about 1.5 mM calcium chloride or any other suitable pharmaceutically accepted carrier. After reconstitution or mixing, the material should be sonicated or vortexed and tested for surface tension lowering capacity and adsorption on a Wilhelmy balance or other surface tension measuring devices. Adsorption studies can be conducted by the methodology disclosed by Notter et al, *Chem. Phys. Lipids,* 33:67–80, 1983 and Ross et al, Phospholipid Binding and Biophysical Activity of Pulmonary Surfactant-Associated Protein (SAP)-35 and Its Non-Collagenous COOH-terminal Domains, 261(30):14283–14291, 1986, in which they are incorporated herein by reference in their entireties.

A phospholipid mixture (SM) containing about 65% dipalmithoylphosphatidylcholine (DPPC), about 20% egg-phosphatidycholine (PC), about 7.5% egg-phosphatidyglycerol (P6) and about 7.5% soy-phosphatidylinositol (PI) is combined with SAP-6-Val proteins and tested in a Wilhelmy balance and nitrogen bubble surfactometer. The SAP-6-Val protein is adsorbed rapidly, lowers surface tension to about 30–47 dynes/cm and is found to be more active than the phospholipid mixture or SAP-35, the major surfactant-associated glycoprotein, mixed with the same phospholipid mixture tested in identical fashion. See Tables II–IV. The methods employed to generate Tables II–IV can be found in detail in Notter et al and Ross et al referenced hereinabove.

TABLE II

ADSORPTION FACILITY OF A SYNTHETIC LIPID MIXTURE (SM)*, A SYNTHETIC LIPID MIXTURE (SM) COMBINED WITH SAP-35, AND A SYNTHETIC LIPID MIXTURE (SM) COMBINED WITH SAP-6 PROTEINS

| Mixture | Lipid Concentration (mg lipid/ml subphase) | Adsorption Surface Pressure $\pi$ at time | | | |
|---|---|---|---|---|---|
| | | t = 0 min | 5 min | 10 min | 15 min |
| SM | 0.6 mg/ml | 1 dyne/cm | 1 | 1 | 3 |
| SM + SAP-35** (canine) | 0.6 mg/ml | 20 dynes/cm | 22 | 22 | 22 |
| SM + | 0.6 mg/ml | 43 dynes/cm | 45 | 45 | 45 |

TABLE II-continued

ADSORPTION FACILITY OF A SYNTHETIC LIPID MIXTURE (SM)*, A SYNTHETIC LIPID MIXTURE (SM) COMBINED WITH SAP-35, AND A SYNTHETIC LIPID MIXTURE (SM) COMBINED WITH SAP-6 PROTEINS

| Mixture | Lipid Concentration (mg lipid/ml subphase) | Adsorption Surface Pressure $\pi$ at time | | |
|---|---|---|---|---|
| | | t = 0 min | 5 min | 10 min | 15 min |
| SAP-6** Proteins (human) | | | | | |

*SM is a synthetic lipid mixture composed of DPPC:egg-PC:egg-PG:soy-PI 65:20:7.5:7.5.
**SAP-35 and SAP-6 proteins have been added in similar molar ratios.

TABLE III

Adsorption of Delipidated SAP-35 and Various Segments and SAP-6-Val Combined with a Synthetic Phospholipid Mixture

| Surfactant Mixture* | **Surface Pressure $\pi$ (dynes/cm) | | | | | |
|---|---|---|---|---|---|---|
| | 0 min | 5 min | 10 min | 15 min | 20 min | 30 min |
| 1. SM | 1 | 1 | 1 | 3 | 3 | |
| 2. SM + Ovalbumin | 1 | 2 | 4 | 5 | 5 | |
| 3. SM + SAP-35 | 9 | 13 | 14 | 15 | 18 | |
| 4. SM + SAP-18 | 8 | 16 | 17 | 17 | 18 | |
| 5. SM + SAP-21 | 2 | 4 | 6 | 7 | 9 | |
| 6. Natural LS | 17 | 46 | 46 | 47 | 47 | |
| 7. SM + Canine SAP-6-Val (25 μg) | 19 | 26 | 29 | 31 | 33 | 37 |
| 8. SM + Canine SAP-6-Val (50 μg) | 37 | 47–48 | 47–48 | 47–48 | 47–48 | |
| 9. SM + Canine SAP-6-Val (100 μg) | 46 | 47 | 47 | 47 | 47 | |

*Delipidated proteins studied are glycoproteins SAP-35, SAP-21 and SAP-18 and canine hydrophobic protein SAP-6-Val. Each of these proteins are combined with a synthetic phospholipid mixture (SM) composed of DPPC:egg-PC:egg-PG:soy-PI 65:20:7.5:7.5. Natural LS (lipid-surfactant) represents optimally active surfactants; ovalbumin is used as a non-specific protein control. Phospholipid concentration for all adsorption experiments is about 0.063 mg/ml 0.15 M NaCl with about 1.4 mM $CaCl_2$; temperature = 35 ± 2° C.. For cases 2–5, the lipid to protein ratio is (wt/wt) 99/1 to 98/2. All mixtures are dispersed by vortexing at room temperature except natural LS (resuspended).
**Surface pressure $\pi$ is the amount of surface tension lowering below that of the pure subphase. The $\pi$ value at 0 min. is that measured within 10 seconds after addition of a bolus of surfactant dispersion to the stirred subphase at time zero. Values given for 1–6 are the means of 4–10 experiments with SEM (standard error of measure) always less than 3 dynes/cm, except for SAP-18 data which are the mean of 2 experiments with a deviation of ±0.5 dynes/cm about the mean.

TABLE IV

Dynamic Surface Tension Lowering During Dynamic Compression on an Oscillating Bubble

| Surfactant Dispersion* | Dispersion Conc. (mg lipid/ml) | Minimum Surface Tension $\pi$ After Cycling (dynes/cm) For | | | | |
|---|---|---|---|---|---|---|
| | | 0.5 min | 2 min | 5 min | 10 min | 11 min |
| 1. SM | 1 mg/ml | 55 | 21 | 21 | 21 | |
| 2. Egg-PC | 1 mg/ml | 53 | 42 | 27 | 22 | |
| 3. SM + SAP-35 | 1 mg/ml | 36 | 36 | 36 | 36 | |
| 4. SM + SAP-35 | 2 mg/ml | 35 | 23 | 21 | 21 | |
| 5. SM + SAP-21 | 1 mg/ml | 54 | 47 | 47 | 42 | |
| 6. LS | 1 mg/ml | 16 | 10 | 2 | 1 | |
| 7. SM + Canine SAP-6-Val (25 μg) | 1 mg/ml | 15 | 15 | 14 | 3 | 1 |
| 8. SM + Canine SAP-6-Val (25 μg) | .5 mg/ml | 17 | 16 | 16 | 16 | 16 |
| 9. SM + Canine SAP-6-Val (25 μg) | 2 mg/ml | 16 | 9 | 4 | 3 | 1 |
| 10. SM + Canine SAP-6-Val (50 μg) | .5 mg/ml | 16 | 15 | 1 | 1 | etc. |
| SM + Canine SAP-6-Val (50 μg) | 1 mg/ml | 15 | 0 | 0 | 0 | etc. |
| SM + Canine SAP-6-Val (50 μg) | 2 mg/ml | 15 | 13 | 1 | etc. | etc. |

*Surfactant dispersions are studied on the oscillating bubble at about 37° C., about 100% humidity, cycling rate about 20 cpm and area compression about 50%. The concentration is 1 or 2 mg lipid/ml bubble subphase as noted. Natural LS (lipid-surfactant) represents active lung surfactant preparation against which to compare the lipid-protein combined mixtures of cases 3–5 and 7–10.

In treating HMD and other related disorders, mixtures containing SAP-6 proteins mixed with naturally occurring or synthetic phospholipids can be instilled intratracheally, for instance, in liquid form or as an aerosol spray in doses of about 0.1% to about 2.0%, by weight, SAP-6 proteins with about 20 to about 100 mg phospholipid per kilogram for treatment or prevention of HMD and other related disorders.

Another utility for SAP-6 proteins is in the preparation of antibodies or antisera against them. Immunochemical methods can be used for detecting and determining SAP-6 proteins, for example, in a fraction from a separation operation, since SAP-6 proteins have antigenic properties.

Immunoblot and ELISA analysis can be used for immunological detection and quantification or other immunological assays of SAP-6 proteins.

An antiserum which can be used for this purpose can be obtained as follows: antisera with which purified SAP-6 proteins can be detected can be obtained by immunization of albino rabbits with repeated injections of delipidated purified SAP-6 proteins and Freund's complete adjuvant. Usable antisera should be obtainable after four injections with approximately 100 micrograms of the delipidated SAP-6 proteins per injection. The antigen used should contain purified SAP-6 proteins assessed by silver staining analysis after one dimension SDS-PAGE. Hybridoma monoclonal antibodies and polyclonal antibodies can also be produced and used.

The detection and determination of SAP-6 proteins by immunological methods is of diagnostic importance. In normal situations, since SAP-6 proteins occur in some tissues of the human body, for example, lung tissue, lung lavage and amniotic fluid, SAP-6 proteins can be detected. In illnesses associated with SAP-6 proteins, the proteins will not appear or will appear in altered concentrations in the serum, tissue, such as the lungs, or other body fluids. The detection or lack of detection of these proteins can be useful for diagnostic determination of an illness or for monitoring the course of a -continued Val—Val—Val—Val—Leu—

Ile—Val—Val—Val—Ile—

Val—Gly—Ala—Leu—Leu—

Met—Gly—Leu.

7. A lung specific hydrophobic surfactant-associated recombinant protein of claim 1, said recombinant protein having a molecular weight of about 3,500–4,000 daltons as determined by tricine-SDS-PAGE, said recombinant protein enhancing surfactant-like activity of phospholipids in lungs of an animal and comprising the following amino acid sequence which corresponds to human:

—Phe—(Gly) —Ile—Pro—Cys—Cys—Pro—
(Arg) (Pro)
(Ile)
(Leu)

Val—Asn—Leu—Lys—Arg—

Leu—Leu—Ile—Val—Val—

Val—Val—Val.

8. A lung specific hydrophobic surfactant-associated recombinant protein of claim 1, said recombinant protein having a molecular weight of about 3,500–4,000 daltons as determined by tricine-SDS-PAGE, said recombinant protein enhancing surfactant-like activity of phospholipids in lungs of an animal and comprising the following amino acid sequence which corresponds to bovine:

Leu—Ile—Pro—Cys—Cys—

Pro—Val—Asn—Ile—Lys—

Arg—Leu—Leu—Ile—Val—

Val—Val—Val—Val—Val—

Leu—Leu—Val—Val—Val.
(Val) (Val)

9. A medicament for reducing or maintaining normal pulmonary surface tension in the alveoli of an animal comprising a SAP-6-Val recombinant protein as recited in claim 1 a phospholipid and a pharmaceutically acceptable carrier, said SAP-6-Val recombinant protein and said phospholipid being present in an effective amount to reduce or maintain normal effective amount to reduce or maintain normal pulmonary surface tension in the alveoli of the animal.

10. A medicament of claim 9, said medicament further including multimers of the SAP-6-Val recombinant protein.

11. A medicament of claim 8, said phospholipid being selected from the group consisting of a synthetic phospholipid and a naturally occurring phospholipid.

12. A medicament of claim 11, said phospholipid being selected from the group consisting of phosphatidylcholine, disaturated phosphatidylcholine, phosphotidylglycerol, dipalmitoylphosphatidylcholine, phosphatidylinositol and mixtures thereof.

13. A preparation for replacing pulmonary surfactant material in lungs of an animal comprising a SAP-6-Val recombinant protein as recited in claim 1 and a phospholipid, both of which are present in said preparation in an effective amount.

14. A preparation of claim 13, said preparation further including multimers of the SAP-6-Val recombinant protein.

15. A preparation of claim 13, said phospholipid being selected from the group consisting of a synthetic phospholipid and a naturally occurring phospholipid.

16. A preparation of claim 15, said phospholipid being selected from the group consisting of phosphatidylcholine, disaturated phosphatidylcholine, phosphatidylglycerol, dipalmitoylphosphatidylcholine, phosphatidylinositol and mixtures thereof.

17. A method of treating or preventing hyaline membrane disease or other syndromes associated with insufficient pulmonary surfactant material in lungs of an animal comprising:
administering to the animal an effective dose comprising a SAP-6-Val recombinant protein as recited in claim 1 and a phospholipid to reduct or maintain normal pulmonary surface tension.

18. A method of claim 17 said administration step comprises administering the effective dose as a liquid or as an aerosol spray.

19. A method of claim 17, the effective dose further including multimers of the SAP-6-Val recombinant protein.

20. A hydrophobic surfactant-associated SAP-6-Val recombinant protein, said SAP-6-Val recombinant protein enhancing surfactant-like activity of phospholipids in lungs of an animal, having a simple molecular weight of about 6,000 daltons determined in a polyacrylamide gel containing sodium dodecyl sulfate and being substantially resistant to protease, endoglycosidase F and collagenase enzymes.

21. A medicament for reducing or maintaining normal pulmonary surface tension in the alveoli of an animal comprising a mixture of a SAP-6-Val recombinant protein as recited in claim 1, phospholipids and a pharmaceutically acceptable carrier, said SAP-6-Val recombinant protein and said phospholipids being present in an effective amount to reduce or maintain normal pulmonary surface tension in the alveoli of the animal.

22. A medicament of claim 21, said phospholipids being selected from the group consisting of synthetic phospholipids, naturally occurring phospholipids and mixtures thereof.

23. A medicament of claim 22, said phospholipids being selected from the group consisting of phosphatidylcholine, disaturated phosphatidylcholine, phosphotidylglycerol, dipalmitoylphosphatidylcholine, phosphatidylinositols and mixtures thereof.

24. A preparation for replacing pulmonary surfactant material in lungs of an animal comprising a mixtures of a SAP-6-Val recombinant protein as recited in claim 1 and phospholipids, both said SAP-6-Val proteins and phospholipids being present in said preparation in an effective amount.

25. A preparation of claim 24, said phospholipids being selected from the group consisting of synthetic phospholipids, naturally occurring phospholipids and mixtures thereof.

26. A preparation of claim 25, said phospholipids being selected from the group consisting of phosphatidylcholine, disaturated phosphatidylcholine, phosphatidylglycerol, dipalmitoylphosphatidylcholine, phosphatidylinositol and mixtures thereof.

27. An isolated lung specific hydrophobic surfactant-associated protein for enhancing surfactant-like activity of phospholipids in lungs of an animal, said protein having a polyvaline domain of valine amino acid residudes, said polyvaline domain containing a first stretch of about six adjacent valine amino acid residues and a second stretch of about three adjacent valine amino acid residues separated from the first stretch by about two hydrophobic amino acid residues, said protein being of a sufficient size for enhancing the surfactant-like activity of phospholipids in lungs of an animal.

28. An isolated lung specific hydrophobic surfactant-associated protein of claim 27, said hydrophobic amino acid residues being selected from a group consisting of leucine, isoleucine and valine.

29. An isolated lung specific hydrophobic surfactant-associated protein of claim 27 wherein said protein is a synthetic protein.

30. A medicament for reducing or maintaining normal pulmonary surface tension in the alveoli of an animal comprising
an isolated lung specific hydrophobic surfactant-associated protein as recited in claim 27, a phospholipid and a pharmaceutically acceptable carrier, said protein and said phospholipid each being present in an effective amount to reduce or maintain normal pulmonary surface tension in the alveoli of the animal.

31. A preparation for replacing pulmonary surfactant material in lungs of an animal comprising an isolated lung specific hydrophobic surfactant-associated protein as recited in claim 27 and a phospholipid, both of which are present in said preparation in an effective amount.

32. A method of treating or preventing hyaline membrane disease or other syndromes associated with insufficient pulmonary surfactant material in lungs of an animal comprising: administering to the animal an effective dose comprising a substantially isolated lung specific hydrophobic surfactant-associated protein as recited in claim 27 to reduce or maintain normal pulmonary surface tension.

33. A substantially pure lung specific hydrophobic surfactant-associated SAP-6 protein composition for enhancing surfactant-like activity of phospholipids in lungs of animals, said SAP-6 protein composition consisting essentially of:
a) a lung specific hydrophobic surfactant-associated SAP-6-Val protein, said SAP-6-Val protein having a polyvaline domain of valine amino acid residues, said polyvaline domain containing a first stretch of about six adjacent valine amino acid residues and a second stretch of about three adjacent valine amino acid residues separated from the first stretch by about two hydrophobic amino acid residues, said SAP-6-Val protein having a molecular weight of about 3,500–4,000 daltons as determined by tricine-SDS-PAGE and a molecular weight of about 6,000 daltons as determined by SDS-PAGE and being substantially resistant to protease, endoglycosidase F and collagenase enzymes; and
b) a second lung specific hydrophobic surfactant-associated SAP-6 protein, said second SAP-6 protein having a molecular weight of about 6,000 daltons as determined by SDS-PAGE and being resistant to protease, endoglycosidase F and collagenase enzymes.

34. A substantially pure SAP-6 protein composition of claim 33, said SAP-6-Val protein having at least about 11 valine amino acids.

35. A substantially pure SAP-6 protein composition of claim 33, said SAP-6-Val protein being a human SAP-6-Val protein.

36. A substantially pure SAP-6 protein composition of claim 33, said SAP-6-Val protein being a synthetic SAP-6Val protein.

37. A substantially pure SAP-6 protein composition of claim 33, said SAP-6-Val protein being a human SAP-6-Val protein comprising the following amino acid sequence:

Ile—Pro—Cys—Cys—Pro—Val—His—Leu—Lys—Arg—Leu—Leu—

Ile—Val—Val—Val—Val—Val—Val—Leu—Ile—Val—Val—Val—

Ile—Val—Gly—Ala—Leu—Leu—Met—Gly—Leu.

38. A substantially pure SAP-6 protein composition of claim 33, said SAP-6-Val protein being a human SAP-6-Val protein comprising the following amino acid sequence:

Ile—Pro—Cys—Cys—Pro—Val—Asn—Leu—Lys—Arg—Leu—Leu—

Ile—Val—Val—Val—Val—Val.

39. A substantially pure SAP-6 protein composition of claim 33, said second SAP-6 protein being a human SAP-6 protein comprising the following amino acid sequence:

Phe—Pro—Ile—Pro—Leu—Pro—Tyr—Cys—Trp—Leu—Cys—Arg—

Ala—Leu.

40. A medicament for reducing or maintaining normal pulmonary surface tension in the alveoli of an animal comprising
a substantially pure SAP-6 protein composition as recited in claim 33, a phospholipid and a pharmaceutically acceptable carrier, said SAP-6 protein composition and said phospholipid each being present in said medicament in an effective amount to reduce or maintain normal pulmonary surface tension in the alveoli of the animal.

41. A preparation for replacing pulmonary surfactant material in lungs of an animal comprising a substantially pure SAP-6 protein composition as recited in claim 33 and a phospholipid, both of which are present in said preparation in an effective amount.

42. A method of isolating from animal pulmonary or amniotic tissue a substantially pure lung specific hydrophobic surfactant-associated SAP-6 protein composition for enhancing surfactant-like activity of phospholipids in lungs of an animal, the substantially pure SAP-6 protein composition consists essentially of a) a lung specific hydrophobic surfactant-associated SAP-6-Val protein, said SAP-6-Val protein having a polyvaline domain of valine amino acid residues, said polyvaline domain including a first stretch of about six adjacent valine amino residues and a second stretch of about three adjacent valine amino acid residues separated from the first stretch by about two hydrophobic amino acid residues, the SAP-6-Val protein having a molecular weight of about 3,500–4,000 daltons as determined by tricine-SDS-PAGE and a molecular weight of about 6,000 daltons as determined by SDS-PAGE and being substantially resistant to protease, endoglycosidase F, and collagenase enzymes, and b) a second lung specific hydrophobic surfactant-associated SAP-6 protein, the second SAP-6 protein having a molecular weight of about 6,000 daltons as determined by SDS-PAGE and being substantially resistant to protease, endoglycosidase F, and collagenase enzymes, said method comprising the steps of:

separating from the animal pulmonary or amniotic tissue a cell fraction and a liquid supernatant;

separating from the liquid supernatant a particulate fraction containing the substantially pure SAP-6 protein composition;

separating from the particulate fraction with an organic solvent a liquid fraction which contains the substantially pure SAP-6 protein composition;

concentrating the liquid fraction to generate a concentrate which contains the substantially pure SAP-6 protein composition;

dispersing the concentrate in a second organic solvent to form a dispersion;

applying the dispersion to a separating column;

eluting the separating column with a first eluting solvent comprising an alcohol and chloroform wherein the concentration of alcohol is less than about 40%;

eluting the separating column with a second eluting solvent comprising an alcohol and chloroform wherein the concentration of alcohol in the second eluting solvent ranges from about 40% up to about 100% to isolate in the second eluting solvent the substantially pure SAP-6 protein composition; and isolating the SAP-6 protein composition from the second eluting solvent in substantially pure form.

43. A method of claim 42, said first eluting step comprising:

eluting the separating column in stepwise increments with selected solvents in series wherein the selected solvents comprise an alcohol and chloroform wherein the alcohol concentration in each selected solvent of the series is continuously increased from 0% up to less than about 40% with each of the stepwise increments.

44. A method of claim 42, said second eluting step comprising:

eluting the separating column in stepwise increments with selected solvents in series wherein the selected solvents comprise an alcohol and chloroform wherein the alcohol concentration in each selected solvent of the series is continuously increased from about 40% up to about 100% with each of the stepwise increments.

45. A method of claim 44, the substantially pure SAP-6 protein composition being eluted during said second eluting step in the selected solvents having an alcohol concentration of about 40% up to about 80%.

46. A method of claim 42, said isolating step comprising:

evaporating the second eluting solvent to generate the substantially pure SAP-6 protein composition.

* * * * *